United States Patent [19]

Ramey et al.

[11] 4,191,682
[45] * Mar. 4, 1980

[54] HINDERED PIPERIDINE CARBOXYLIC ACIDS, METAL SALTS THEREOF AND STABILIZED COMPOSITIONS

[75] Inventors: Chester E. Ramey, Spring Valley; John J. Luzzi, Carmel, both of N.Y.

[73] Assignee: Ciba-Geigy Corporation, Ardsley, N.Y.

[*] Notice: The portion of the term of this patent subsequent to Nov. 18, 1992, has been disclaimed.

[21] Appl. No.: 918,211

[22] Filed: Jun. 22, 1978

Related U.S. Application Data

[62] Division of Ser. No. 700,380, Jun. 28, 1976, Pat. No. 4,116,933.

[51] Int. Cl.² .................... C08K 5/34; C07D 211/46
[52] U.S. Cl. .............................. 260/45.8N; 546/5; 546/16; 546/222; 546/242; 260/45.75 R; 260/45.75 Q; 260/45.75 J; 260/45.75 C; 260/45.75 N; 260/45.75 W; 260/45.75 M
[58] Field of Search .................. 260/45.8 N, 45.75 R, 260/45.75 Q, 45.75 J, 45.75 C, 45.75 N, 45.75 W, 45.75 M, 45.8 NP; 546/5, 16, 222, 242

[56] References Cited

U.S. PATENT DOCUMENTS

| | | | |
|---|---|---|---|
| 3,920,661 | 11/1975 | Ramey et al. | 546/5 |
| 3,939,163 | 2/1976 | Ramey et al. | 546/5 |
| 4,031,095 | 6/1977 | Ramey et al. | 546/5 |
| 4,056,507 | 11/1977 | Ramey et al. | 546/5 |
| 4,069,199 | 1/1978 | Ramey et al. | 546/5 |
| 4,089,842 | 5/1978 | Ramey et al. | 546/5 |
| 4,101,509 | 7/1978 | Ramey et al. | 546/5 |
| 4,116,933 | 9/1978 | Ramey et al. | 546/5 |

Primary Examiner—Alan L. Rotman
Assistant Examiner—Robert T. Bond
Attorney, Agent, or Firm—Vincent J. Cavalieri

[57] ABSTRACT

Compounds having the formula

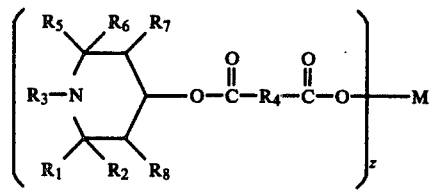

wherein
$R_1$ and $R_2$ are lower alkyl or together lower alkylene,
$R_3$ is hydrogen, alkyl, methoxyethyl, alkenyl, propargyl, benzyl, alkyl substituted benzyl, or acyl,
$R_4$ is alkylene, alkyl-thio-alkyl or alkyl-oxo-alkyl,
M is hydrogen or a metal, and z has a value of from 1 to 4, and either
to 6 carbon atoms, and $R_7$ and $R_8$ are independently hydrogen or alkyl of 1 to 5 carbon atoms, provided that $R_7$ and $R_8$ are not both hydrogen, or
(b) $R_5$ and $R_6$ are together lower alkylene and $R_7$ and $R_8$ are independently hydrogen or alkyl of 1 to 5 carbon atoms, are good light stabilizers. The carboxylic acids are prepared for example, from 2,3,6-trimethyl-2,6-diethylpiperidin-4-ol and sebacic acid to give 2,3,6-trimethyl-2,6-diethyl-4-piperidyl hydrogen sebacate. The metal salts of the acids are readily prepared by reacting the acids or their salts with a reactive form of the metal or metal complex.

17 Claims, No Drawings

HINDERED PIPERIDINE CARBOXYLIC ACIDS, METAL SALTS THEREOF AND STABILIZED COMPOSITIONS

This is a divisional of application Ser. No. 700,380, filed on June 28, 1976 now U.S. Pat. No. 4,116,933.

BACKGROUND OF THE INVENTION

This invention relates to the stabilization of organic material normally tending to deteriorate. In particular, the invention relates to the protection of synthetic polymers against the harmful degradative effects, such as discoloration and embrittlement, caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate, spot and degrade. The rate of air oxidation of polyolefins, such as polyethylene and polypropylene, is materially accelerated by ultraviolet light.

In U.S. Pat. No. 3,120,540 there is discussed the reaction of substituted 4-piperidinol compounds with acid anhydrides having formula

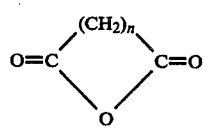

where n is 1 to 4, to yield bis(polymethyl)-4-piperidyl alkanoates. In the example of this patent the salt of 1,2,2,6,6-pentamethyl-4-piperidinol with the acid of formula

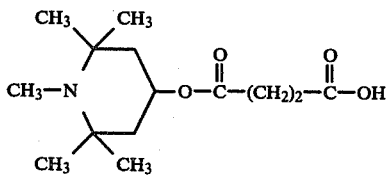

is a plausible intermediate in the synthesis of the bis-(hydrogen sulfate)salt of bis(1,2,2,6,6-pentamethyl-4-piperidyl)succinate. The compounds of U.S. 3,120,540 are taught to possess significant pharmacological activity in lowering blood pressure. We have now found that acid half esters of hindered piperidines stabilize organic substrates against the degradative effect of ultraviolet light.

DETAILED DISCLOSURE

The present invention is accordingly directed to a new class of ultraviolet light stabilizers which consists of a compound of the formula

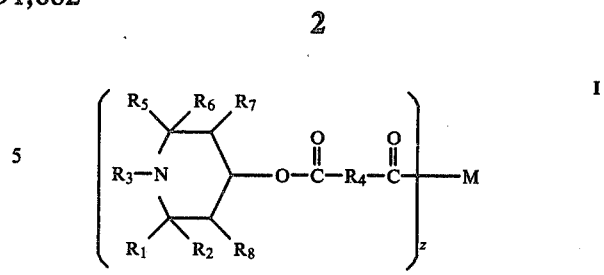

wherein $R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with the a methyl group, $R_3$ is hydrogen, alkyl having 1 to 12 carbon atoms, $\beta$-methoxyethyl, alkenyl having 3 to 4 carbon atoms, propargyl, benzyl, alkyl substituted benzyl or acyl, $R_4$ is straight-or branched-chain alkylene of 1 to 8 carbon atoms, or the group $(CH_2)_m Y (CH_2)_n$ wherein Y is oxygen or sulfur and m and n independently of each other are an integer from 1 to 18, preferably 1 to 8, more preferably 1 to 4.

M is hydrogen or a metal selected from the group consisting of barium, nickel, manganese, calcium, copper, zinc, magnesium, sodium, potassium, cobalt, tin, and dialkyl tin z has a value of from 1 to 4, the value of z being the same as the available valence of M, and either (a) $R_5$ is alkyl of 1 to 6 carbon atoms, preferably 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen, or (b) $R_5$ and $R_6$ together with the carbon to which they are bound form a cyclopentyl or cyclohexyl ring, which is unsubstituted with a methyl group and $R_7$ and $R_8$ are independently hydrogen or alkyl of 1 to 5 carbon atoms.

Examples of $R_1$ and $R_2$ are methyl, ethyl, n-propyl, n-butyl and n-hexyl. Preferably, $R_1$ and $R_2$ are each lower alkyl such as a methyl group. Representative of $R_1$ and $R_2$ together with the carbon to which they are bound as cycloalkyl groups are cyclohexyl, cyclopentyl, 2-methyl-, 3-methyl- and 4-methylcyclohexyl, and 2-methyl- and 3-methylcyclopentyl. The preferred cycloalkyl groups are cyclohexyl and 2-methylcyclohexyl. Most preferably, $R_1$ is methyl and $R_2$ is ethyl.

Substituent $R_3$ can be hydrogen, alkyl having 1 to 12 carbon atoms, preferably alkyl having 1 to 4 carbon atoms, hydrogen and methyl being particularly preferred, $\beta$-methoxyethyl, alkenyl having 3 to 4 carbon atoms, preferably allyl, propargyl, benzyl or alkyl substituted benzyl. Acyl $R_3$ is especially alkanoyl with 1 to 18, especially 2 to 6 carbon atoms, e.g., acetyl, or alkenoyl with 2 to 18 carbon atoms, especially 2 to 6 carbon atoms, e.g., acryloyl or crotonyl.

Examples of $R_3$ are hydrogen, methyl, ethyl, n-propyl, isopropyl, n-butyl, isobutyl, n-hexyl, n-octyl, n-dodecyl, allyl, $\alpha$-methallyl, propargyl, benzyl, $\alpha$-methylbenzyl and $\alpha$, p-dimethylbenzyl.

The preferred alkylene residue $R_4$ is straight-chain alkylene having 1 to 8, more preferably 4 to 8 carbon atoms, or the group $(CH_2)_m Y(CH_2)_n$ wherein Y is oxygen or sulfur and m and n independently of each other are 1 to 2. More preferably, m and n are the same. Another preferred residue represented by $R_4$ is alkylene.

Among the substituents represented by M, hydrogen, nickel and manganese are preferred. More preferably, M is hydrogen or nickel, most preferably nickel. Another preferred substituent represented by M is calcium.

Examples of $R_5$ and $R_6$ are methyl, ethyl, n-propyl, n-butyl and n-hexyl.

Alkyl $R_5$ is especially n-alkyl of 2 to 6 carbon atoms, most preferably ethyl. Alkyl $R_6$ is especially n-alkyl with 1 to 6 carbon atoms, e.g., ethyl, most preferably methyl. Alkyl $R_7$ and $R_8$ are especially n-alkyl, like methyl, but most preferably one of $R_7$ and $R_8$ is hydrogen and the other one is methyl.

Most preferably $R_7$ contains one carbon atom less than $R_5$, and $R_8$ contains one carbon atom less than $R_6$. Also, most preferably, $R_1$ is the same as $R_5$ and $R_2$ is the same as Rhd 6.

Representative of $R_5$ and $R_6$ together with the carbon to which they are bound as cycloalkyl groups are cyclohexyl, cyclopentyl, 2-methyl-, 3-methyl- and 4-methylcyclohexyl, and 2-methyl- and 3-methylcyclopentyl. The preferred cycloalkyl groups are cyclohexyl and 2-methylcyclohexyl.

A preferred group of compounds of formula I are therefore those wherein $R_1$ and $R_5$ are ethyl, $R_2$ and $R_6$ are methyl, one of $R_7$ and $R_8$ is hydrogen and the other is methyl, $R_3$ is hydrogen, methyl, allyl, benzyl, acetyl, acryloyl or crotonyl, and $R_4$, M and z have the above-preferred meanings.

Particularly preferred compounds of the invention have the formula

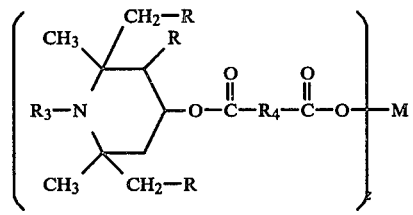

wherein R is lower n-alkyl of 1 to 5 carbon atoms, especially methyl, and $R_3$, $R_4$ and M are as defined above.

This invention also relates to compositions of matter which are stabilized against ultraviolet light deterioriation which comprise a sythetic organic polymer normally subjected to ultraviolet deterioriation containing from about 0.005% to 5% by weight of the polymer of the compounds of formula I and preferably from 0.01 to 2% by weight.

The compounds as represented by formula I, can be used in combination with other light stabilizers such as 2(2-hydroxyphenyl)benzotriazoles, 2-hydroxybenzophenones, nickel complexes and benzoates.

The compounds of this invention are stabilizers for organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, $\alpha$, $\beta$-unsaturated acids, $\alpha$, $\beta$-unsaturated esters, $\alpha$, $\beta$-unsaturated ketones, $\alpha$, $\beta$-unsaturated aldehydes and unsaturated hydrocarbons such as butadienes and styrene; poly-$\alpha$-olefins such as high and low density polyethylene, cross-linked polyethylene, polypropylene, poly(4-methyl)-1-pentene and the like, including copolymers of $\alpha$-olefins; such as ethylene-propylene copolymers, and the like; polydienes such as polybutadiene, polyisoprene, and the like, including copolymers with other monomers; polyurethanes such as are prepared from polyols and organic polyisocyanates, and polyamides such as polyhexamethylene adipamide and polycarbonates such as those prepared from bisphenol-A and phosgene; polyacetals polyacetals and polyesters such as polyethylene terephthalate polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., ethylene diazelate, pentaerythrityl tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like; salts of fatty acids such as soaps and the like; and alkylene glycols, e.g., 2-methoxyethanol, 2-(2-methoxyethoxy)ethanol, triethylene glycol, octaethylene glycol, dibutylene glycol, dipropylene glycol and the like.

The compounds of this invention are particularly useful as UV light stabilizers, especially for the protection of polyolefins, for instance, polyethylene, polypropylene, poly-1-butene, poly-1-pentene, poly-3-methyl-1-butene, poly-4-methyl-1-pentene, various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-$\beta$-thiodipropionate (DSTDP), dilauryl-$\beta$-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and other chemicals used in rubber compounding, plasticizers, color stabilizers, di- and tri-alkyl- and -alkylphenyl-phosphites, as well as other phosphites, e.g., distearyl pentaerythritol diphosphite, heat stabilizers, ultraviolet light stabilizers, antiozants, dyes, pigments, metal chelating agents, dyesites and the like. Often combinations with other additives such as those mentioned above, particularly the sulfur containing esters, the phosphites and/or the ultraviolet light stabilizers, will produce superior results in certain applications compared with those expected by the properties of the individual components.

The following formula represents co-stabilizers which are in certain instances very useful in combination with the stabilizers of this invention:

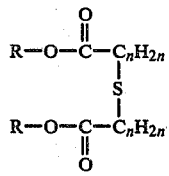

wherein R is an alkyl group having from 6 to 24 carbon atoms; and n is an integer from 1 to 6. Especially useful compounds of these are dilauryl-$\beta$-thiodipropionate and distearyl-$\beta$-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidation degradation. The amount of antioxidant required will be comparable to that of the actinic stabilizer. Namely, from about 0.005% to 5% and preferably from 0.01% to 2% by weight. Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Among these phenolic antioxidants are included the following:

di-n-octadecyl(3-tert-butyl-4-hydroxy-5-methylbenzyl)-malonate
2,6-di-tert-butylphenol
2,2'-methylene-bis(6-tert-butyl-4-methylphenol)
2,6-di-tert-butylhydroquinone
octadecyl-(3,5-di-tert-butyl-4-hydroxybenzyl-thio)acetate
1,1,3-tris(3-tert-butyl-6-methyl-4-hydroxyphenyl)butane
1,4-bis(3,5-di-tert-butyl-4-hydroxybenzyl)2,3,5,6-tetramethylbenzene
2,4-bis(3,5-di-tert-butyl-4-hydroxyphenoxy)-6-(n-octylthio)-1,3,5-triazine
2,4-bis-(4-hydroxy-3,5-di-tert-butylphenoxy)-6-(n-octylthioethylthio)-1,3,5-triazine
2,4-bis-(n-octylthio)-6-(3,5-di-tert-butyl-4-hydroxyanilino)-1,3,5-triazine
2,4,6-tris-(4-hydroxy-3,5-di-tert-butylphenoxy)-1,3,5-triazine
n-octadecyl-3-(3,5-di-tert-butyl-4-hydroxyphenyl)propionate
n-octadecyl-3,5-di-tert-butyl-4-hydroxybenzoate
2-(n-octylthio)ethyl-3,5-di-tert-butyl-4-hydroxybenzoate
n-octadecanoyl-di-2-[3-(3,5-di-tert-butyl-4-hydroxyphenyl)propionyloxy]ethylamine
1,2-propylene di-[3-(3,5-di-tert-butyl-4-hydroxyphenyl)propionate]
pentaerythrityl tetra [3-(3,5-di-tert-butyl-4-hydroxyphenyl)propionate]
di-octadecyl-(3,5-di-tert-butyl-4-hydroxy-benzyl)phosphonate
di-octadecyl-1-(3,5-di-tert-butyl-4-hydroxyphenyl)ethanephosphonate The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herein by reference, are disclosed in greater detail in the following patents:

Netherlands Patent Specification No. 67/1119, issued Feb. 19, 1968; Netherlands Patent Specification No. 68/03498 issued Sept. 18, 1968; U.S. Pat. Nos. 3,255,191; 3,330,859; 3,644,482; 3,281,505; 3,531,483; 3,285,855; 3,364,250; 3,368,997; 3,356,944 and 3,758,549.

The compounds of this invention may be prepared by reacting a piperidinol of the formula

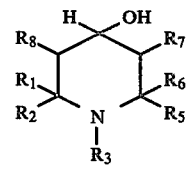

wherein $R_1$, $R_2$, $R_3$, $R_5$, $R_6$, $R_7$, and $R_8$ are as defined above in formula I via a usual esterification procedure with a diacid of the formula

wherein $R_4$ is as defined above, or conveniently with an acid anhydride thereof such as succinic anhydride, glutaric anhydride, diglycolic anhydride and the like. In the process of reacting an acid of formula III with a compound of formula II, the esterification catalyst is preferably a neutral catalyst, for instance a tetra-alkyl titanate.

The acids and acid anhydrides which are reacted with the compounds of formula II may be prepared by methods well known in the art.

The metal salts of the present invention can be prepared by treating the hindered piperidine carboxylic acids of formula I with a reactive form of the metal or metal complex, e.g., sodium hydroxide or the like. Alternatively, and preferably in the case of metal complexes and metals other than the alkali metals, a double decomposition is employed. Thus for example, a sodium salt of the present invention is treated with nickel chloride. In a similar fashion use of other halides such as manganese dichloride, barium chloride and the like results in formation of the corresponding metal derivative.

The compounds of formual II may be prepared similarly to procedures presented in the published German Patent Application DT-OS No. 2,352,658, especially by reducing a corresponding 4-piperidone by catalytic hydrogenation or, e.g., with lithium aluminum hydride. The corresponding 4-ketone can be prepared by reacting an aliphatic ketone, this being a higher homologue of acetone, with ammonia, e.g., 2,3,6-trimethyl-2,6-diethyl-4-oxopiperidine is obtained from methylethylketone and ammonia, similar to W. Traube in Chem. Ber. 41 (1908), 777. The corresponding 4-ketone can also be obtained by hydrolysis of an alkyl-substituted tetrahydropyridine in the presence of an acidic catalyst, similar to U.S. Patent No. 3,513,170. Corresponding 4-ketones having different substituents in the 2- and 6-positions can be obtained by reacting first a ketone $R_5$—CO—$R_6$ with ammonia and hydrolyzing the formed pyrimidine derivative to give an amino ketone $NH_2$—$C(R_5R_6)$—$CH(R_7)$—CO—$CH_2R_8$ as described in Helv. Chim. Acta 30 (1947), 1114. In a second step, this amino ketone is reacted with ammonia and a second ketone $R_1$—CO—$R_2$, resulting in a pyrimidine derivative as described in Monatshefte Chemie 88(1957), 464. From this the 4-ketone can be obtained by hydrolysis. Similar methods in preparing alkylated 4-piperidones are described in published German Patent Application Nos. 2,429,745; 2,429,746; 2,429,935; 2,429,936 and 2,429,937.

Compounds of the type wherein both $R_1$ and $R_2$ and $R_5$ and $R_6$ together with the carbons to which they are attached form cycolhexyl or cyclopentyl rings can be prepared by the method of T. Yoshioka, S. Higashida and K. Murayama, Bull. Chem. Soc. Japan 45 636–638 (1972) with subsequent reduction of the ketone with hydrogen and a catalyst or sodium borohydride to the alcohol.

Compounds of formula I with $R_3$ being acyl may be prepared by acylation of the corresponding N—H compounds with the corresponding carboxylic acid, anhydride, ester or halide as known per se.

The following examples, presented for illustration and not limitation, will further serve to typify the nature of the present invention.

EXAMPLE 1

2,6-Diethyl-2,3,6-trimethylpiperidin-4-ol

In a 2-liter, 3-necked flask equipped with a stirrer, condenser, thermometer and nitrogen inlet were placed 197.3 g. (1.0 moles) of 2,6-diethyl-2,3,6-trimethylpiperidin-4-one, 500 ml of 2N sodium hydroxide and 500 ml of absolute ethanol. To the stirred reaction mixture, maintained under nitrogen, was added portionwise 18.92 m (0.5 moles) of sodium borohydride over a 1½ hour period. The reaction mixture was then stirred overnight at room temperature. The reaction mixture was decanted into a 4-liter separatory funnel and 2 liters of water were added. The aqueous layer was separated and the organic layer diluted with 500 ml of ether. The ether solution was washed with 2×1 l water. The first aqueous layer was extracted with 2×50 ml of ether, then the combined ether extracts were washed with 500 ml of water. The ether layers were combined, dried over 4A molecular sieves and evaporated under reduced pressure, giving 187.4 g of the desired 2,6-diethyl-2,3,6-trimethylpiperidin-4-ol which was purified further by vacuum distillation, b.p. 111°–115°/6 mm.

EXAMPLE 2

O-mono-(2',6'-diethyl-2',3',6'-trimethylpiperidyl-4')2-methyl succinate

A. In a 300 ml 3-necked flask equipped with a stirrer, condenser with drying tube, thermometer and nitrogen inlet were placed 19.93 g (0.1 moles) of 2,6-diethyl-2,3,6-trimethylpiperidin-4-ol, and 150 ml of dry toluene. To the stirred solution was added 11.4 g (0.1 moles) of 2-methyl succinic anhydride. The reaction mixture was heated under reflux for 5 hours. At the end of this time, the reaction mixture was cooled to room temperature, evaporated under reduced pressure and further dried at 100° C. and 1 mm for 4 hours, yielding 33.5 g of product as a tan glass, which on titration with $HClO_4$/HOAc gave an equivalent weight of 341.3 (theory 313.4).

B. By following the above procedure (A) and substituting for the 2-methyl succinic anhydride and equivalent amount of succinic anhydride there is obtained O-mono(2,6-diethyl-2,3,6-trimethylpiperidyl-4)succinate.

C. By following the above procedure (A) and substituting for the 2,6-diethyl-2,3,6-trimethylpiperidin-4-ol an equivalent amount of the following reagents:

(a) 1-n-dodecyl-2,6-diethyl-2,3,6-trimethylpiperidin-4-ol
(b) 1-benzyl-2,6-diethyl-2,3,6-trimethylpiperidin-4-ol
(c) 2,6-diethyl-1,2,3,6-tetramethylpiperidin-4-ol there are respectively obtained:

(a) O-mono(1'-n-dodecyl-2',6'-diethyl-2',3',6'-trimethylpiperidyl-4')2-methyl succinate
(b) O-mono(1'-benzyl-2',6'-diethyl-2',3',6'-trimethylpiperidyl-4')2-methyl succinate
(c) O-mono(2',6'-diethyl-1',2',3',6'-tetramethylpiperidyl-4')2-methyl succinate.

EXAMPLE 3

O-mono-(2',6'-diethyl-2',6'-trimethylpiperidyl-4')3-methyl glutarate

A. In a 300 ml 3-necked flask equipped with a stirrer, condenser with drying tube, thermometer and nitrogen inlet were placed 19.93 g (0.1 moles) of 2,6-diethyl-2,3,6-trimethylpiperidin-4-ol, and 150 ml of dry toluene. To the stirred solution was added 12.8 g (0.1 moles) of 3-methyl glutaric anhydride and the reaction mixture was heated under reflux for 6 hours. The reaction mixture was cooled to room temperature, evaporated under reduced pressure and further dried at 100° C. and 0.1 mm for 4 hours, yielding 35.1 g of product as a tacky yellow semi-solid which had an equivalent weight of 352.4 (theory 327.4) by titration with $HClO_4$/HOAc.

B. By following the above procedure (A) and substituting for the 3-methyl glutaric anhydride an equivalent amount of cyclic adipic anhydride (prepared from adipic acid and acetic anhydride by the procedure of J. W. Hill, J. Am. Chem. Soc. 52 4110 (1930) there is obtained O-mono(2,6-diethyl-2,3,6-trimethylpiperidyl-4)-adipate.

EXAMPLE 4

Ni(II) Bis[O-mono(2',6'-diethyl-2',3',6'-trimethylpiperidyl-4')2-methyl succinate]

A. In a 250 ml erlenmeyer flask equipped with a magnetic stirrer were placed 10.2 g (0.03 moles) of O-mono-2',6'-diethyl-2',3',6'-trimethylpiperidyl-4') 2-methyl succinate, 30 ml of 1.0 N KOH in methanol and 100 ml of methanol and the mixture was stirred until solution was complete. To the reaction mixture was added portionwise with stirring a solution of 3.57 g (0.015 moles) of $NiCl_2·6H_2O$ in 20 ml of methanol, and the mixture was stirred at room temperature for 2 hours. The reaction mixture was then filtered, and the filtrate evaporated under reduced pressure. The residue was dissolved in 150 ml of benzene, the benzene solution was filtered, and evaporated under reduced pressure, giving the desired Ni compound as a green solid of the following elemental composition:

Calculated for $C_{34}H_{60}N_2O_8Ni$, F.W. 683.55. Calculated: C, 59.74; H, 8.85; N, 4.10; Ni, 8.59. Found: C, 58.71; H, 8.91; N, 4.04; Ni, 8.44. C, 58.93; H, 9.05; N, 4.01.

B. By following the above procedure (A) and substituting for the $NiCl_2·6H_2O$ an equivalent amount of $CaCl_2$, there was obtained Ca(II) Bis [O-mono(2',6'-diethyl-2',3',6'-trimethylpiperidyl-4')2-methyl succinate], a tan solid, of the following elemental composition:

Calculated for $C_{34}H_{60}N_2O_8Ca$, F.W. 664.92. Calculated: C, 61.41; H, 9.10; N, 4.21; Ca, 6.03. Found: C, 61.13; H, 9.37; N, 4.11; Ca, 6.40.

C. By following the above procedure (A) and substituting for the O-mono(2',6'-diethyl-2,3,6-trimethyl-piperidyl-4')2-methyl succinate an equivalent amount of the following reagents:

(a) O-mono(2',6'-diethyl-1',2',3',6'-tetramethylpiperidyl-4')2-methyl succinate
(b) O-mono(1'-benzyl-2',6'-diethyl-2',3',6'-trimethylpiperidyl-4')2-methyl succinate
(c) O-mono(2,6-diethyl-2,3,6-trimethylpiperidyl-4)adipate there are respectively obtained:

(a) Ni(II) Bis[O-mono(2',6'-diethyl-1',2',3',6'-tetramethylpiperidyl-4')2-methyl succinate]
(b) Ni(II) Bis[O-mono(1'-benzyl-2',6'-diethyl-2', 3',6'-trimethylpiperidyl-4')2-methyl succinate]
(c) Ni(II) Bis [O-mono(2',6'-diethyl-2',3',6'-trimethylpiperidyl-4')adipate]

EXAMPLE 5

Co(II) Bis[O-mono(2',6'-diethyl-2',3',6'-trimethylpiperidyl-4')3-methyl glutarate]

A. In a 250 ml erlenmeyer flask equipped with a magnetic stirrer were placed 10.57 g (0.03 moles) of O-mono-2',6'-diethyl-2',3',6'-trimethylpiperidyl-4') 3-methyl glutarate, 30 ml of 1N KOH in methanol and 100 ml of methanol. The reaction mixture was stirred until solution was complete and a solution of 3.57 g (0.015 moles) of $CoCl_2·6H_2O$ in 25 ml of methanol was added portionwise with stirring. The reaction mixture was stirred for 2 hours at room temperature, filtered, and the filtrate evaporated under reduced pressure. The residue was dissolved in 150 ml of benzene, the solution filtered, and the filtrate dried over 4A molecular seives. The benzene solution was then evaporated under reduced pressure, giving 10.42 g of the desired Co compound as a purple solid of the following elemental composition:

Calculated for $C_{36}H_{64}N_2O_8Co$, F.W. 711.84. Calculated: C, 60.74; H, 9.06; N, 3.94; Co, 8.28. Found: C, 60.02; H, 9.25; N, 3.78; Co, 7.90. C, 59.71; H, 9.03; N, 3.79.

B. By following the above procedure (A) and substituting for the $CoCl_2·6H_2O$ an equivalent amount of $MgCl_2·6H_2O$, there was obtained Mg(II) Bis [O-mono (2',6'-diethyl-2',3',6'-trimethylpiperidyl-4')3-methyl glutarate], a yellow solid, of the following elemental composition:

Calculated for $C_{36}H_{64}N_2O_8Mg$, F.W. 677.2. Calculated: C, 63.85; H, 9.53; N, 4.14; Mg, 3.59. Found: C, 63.09; H, 9.22; N, 4.09; Mg, 3.59. C, 63.37; H, 9.28; N, 4.04.

EXAMPLE 6

By following the procedure of Example 4 and substituting for the $NiCl_2·6H_2O$ and equivalent amount of the following metal chlorides:

(a) manganese chloride
(b) zinc chloride
(c) barium chloride
(d) tin (IV) chloride
(e) cupric chloride there are respectively obtained:

(a) manganese complex of O-mono(2', 6'-diethyl-2',3',6'-trimethylpiperidyl-4')2-methyl succinate
(b) zinc complex of O-mono(2',6'-diethyl-2',3',6'-trimethylpiperidyl-4')2-methyl succinate
(c) barium complex of O-mono(2',6'-diethyl-2',3',6'-trimethylpiperidyl-4')2-methyl succinate
(d) tin complex of O-mono(2',6'-diethyl-2',3',6'-trimethylpiperidyl-4')2-methyl succinate
(e) cupric complex of O-mono(2',6'-diethyl-2',3',6'-trimethylpiperidyl-4')2-methyl succinate

EXAMPLE 7

O-mono-(2,6-diethyl-2,3,6-trimethyl-piperidyl-4)sebacate

A. In a 1-liter, 3-necked flask equipped with a stirrer, thermometer, condenser with drying tube and Dean-Stark trap and nitrogen inlet were placed 20.23 g (0.1 moles) of sebacic acid, 19.93 g (0.1 moles) of 2,6-diethyl-2,3,6-trimethylpiperidin-4-ol and 300 ml of mesitylene, The stirred reaction mixture was heated to 100°, and 1.42 g (0.005 moles) of $Ti(Oipr)_4$ (tetraisopropyl titanate) was added. The reaction mixture was heated to reflux, and 28 ml of distillate was removed from the Dean-Stark trap. The reaction mixture was heated at reflux for 6 hours, during which time 0.8 ml of water accumulated in the trap. An additional 0.5 g of $Ti(Oipr)_4$ was added and the reflux resumed for 4 hours, during which time an additional 0.4 ml of water accumulated. The reaction mixture was then cooled to room temperature, decanted from the insoluble residue, and evaporated under reduced pressure. The residue from the evaporation was added to 150 ml 0.5N NaOH, and the basic solution was extracted with 1×125 and 2×50 ml of ether. The aqueous layer was acidified to pH 1.5–2.0 by the addition of 55 ml of 4N HCl, which resulted in the formation of a separate phase. The acidified aqueous mixture was extracted with 125 ml of ether, and the ether layer separated from the aqueous phase and a third phase. The aqueous layer and third phase were neutralized to pH 7.2—7.6 by the addition of 35 ml of 4N NaOH, and the remaining ether removed by blowing a stream of nitrogen through the aqueous mixture. The aqueous mixture was extracted with 3×100 ml of CHCl$_3$ The CHCl$_3$ extracts were combined, dried over 4A molecular sieves and evaporated under reduced pressure. The residue was further dried to constant weight at 100°/0.1 mm, giving 17.2 g of the desired half ester, as a tan resin, which when analyzed by titration with HClO$_4$/HOAc, gave an equivalent weight of 390.7 (theory 383.6) and had the following elemental analysis:

Calculated for $C_{22}H_{44}NO_4$, F.W. 383.6. Calculated: C, 68.89; H, 10.77; N, 3.65. Found: C, 68.73; H, 10.40; N, 3.35.

B. By following the above procedure (A) and substituting for the sebacic acid an equivalent amount of:

(a) pimelic acid
(b) tetramethyl succinic acid
(c) azelaic acid
(d) thiodipropionic acid
(e) suberic acid
(f) thiodiglycolic acid there are respectively obtained:

(a)    O-mono(2,6-diethyl-2,3,6-trimethylpiperidyl-4)pimelate
(b) O-mono(2,6-diethyl-2,3,6-trimethylpiperidyl-4)tetramethyl succinate
(c) O-mono(2,6-diethyl-2,3,6-trimethylpiperidyl-4)azelate
(d) O-mono(2,6-diethyl-2,3,6-trimethylpiperidyl-4)thiodipropionate
(e) O-mono(2,6-diethyl-2,3,6-trimethylpiperidyl-4)suberate
(f) O-mono(2,6-diethyl-2,3,6-trimethylpiperidyl-4)thiodiglycolate C. By essentially following the above procedure (A), and substituting for the reactants appropriate quantities of the following reagents:

(a) 1-n-dodecyl-2,6-diethyl-2,3,6-trimethylpiperidin-4-ol and sebacic acid
(b) 1-benzyl-2,6-diethyl-2,3,6-trimethylpiperidin-4-ol and azelaic acid
(c) 1-allyl-2,6-diethyl-2,3,6-trimethylpiperidin-4-ol and suberic acid there are respectively obtained:

(a) O-mono(1-n-dodecyl-2,6-diethyl-2,3,6-trimethylpiperidyl-4)sebacate
(b) O-mono(1-benzyl-2,6-diethyl-2,3,6-trimethylpiperidyl-4)azelate
(c) O-mono(1-allyl-2,6-diethyl-2,3,6-trimethylpiperidyl-4)suberate

EXAMPLE 8

Ni(II)
Bis[O-mono(2,6-diethyl-2,3,6-trimethylpiperidyl-4)sebacate]

A. In a 125 ml erlenmeyer flask equipped with a magnetic stirrer were placed 3.84 g (0.01 moles) of O-mono(2,6-diethyl-2,3,6-trimethylpiperidyl-4)sebacate 5 ml of 2N NaOH and 25 ml of water. The mixture was stirred for 1 hour at room temperature until the reaction became homogeneous. To the stirred solution was added a solution of 1.19 g (0.005 moles) of NiCl$_2$·6H$_2$O in 5ml of water portionwise. To the stirred solution was added 50 ml of ether and the reaction mixture was allowed to stir for 1 hour. The reaction mixture was transferred to a separatory funnel and the ether layer separated. The aqueous layer was washed with 25 ml of ether, the ether layers combined, dried over 4A molecular sieves, and evaporated to dryness under reduced pressure, giving the desired Ni salt as a green rubbery solid of the following elemental composition:

Calculated for $C_{44}H_{86}N_2O_8Ni$, F.W. 829.85. Calculated: C, 63.68; H, 10.45; N, 3.38; Ni, 7.07. Found: C, 61.53, H; 9.22; N, 3.22; Ni, 8.10.

B. By following the above procedure (A) and substituting for the O-mono(2,6-diethyl-2,3,6-trimethylpiperidyl-4)sebacate, an equivalent amount of:

(a)    O-mono(2,6-diethyl-2,3,6-trimethylpiperidyl-4)pimelate
(b)    O-mono(2,6-di-n-butyl-2,6-dimethyl-3-n-propyl piperidyl-4) tetramethyl succinate
(c) O-mono(2,6-diethyl-2,3,6-trimethylpiperidyl-4)thiodiglycolate
(d)    O-mono(1-n-dodecyl-2,6-diethyl-2,3,6-trimethylpiperidyl-4)sebacate
(e) O-mono(1-benzyl-2,6-diethyl-2,3,6-trimethylpiperidyl-4)azelate
(f)    O-mono-(1-allyl-2,6-diethyl-2,3,6-trimethylpiperidyl-4)suberate there are respectively obtained:

(a) nickel complex of O-mono(2,6-diethyl-2,3,6-trimethylpiperidyl-4)pimelate
(b) nickel complex of O-mono(2,6-di-n-butyl-2,6-dimethyl-3n-propylpiperidyl-4)tetramethyl succinate
(c) nickel complex of O-mono(2,6-diethyl-2,3,6-trimethylpiperidyl-4)thiodiglycolate
(d) nickel complex of O-mono(1-n-dodecyl-2,6-diethyl-2,3,6-trimethylpiperidyl-4)sebacate
(e) nickel complex of O-mono(1-benzyl-2,6-diethyl-2,3,6-trimethylpiperidyl-4)azelate
(f) nickel complex of O-mono(1-allyl-2,6-diethyl-2,3,6-trimethylpiperidyl-4)suberate.

EXAMPLE 9

Mg(II)
Bis[O-mono(2,6-diethyl-2,3,6-trimethylpiperidyl-4)sebacate]

A. In a 125 ml erlenmeyer flask equipped with a magnetic stirrer were placed 3.84 g (0.01 moles) of O-mono(2,6-diethyl-2,3,6-trimethylpiperidyl-4) sebacate, 10 ml of 1N KOH in methanol and 25 ml of methanol. The mixture was stirred until solution was complete, and a solution of 1.02 g (0.005 moles) of MgCl$_2$·6H$_2$O in 5 ml of methanol was added portionwise. An additional 25 ml of methanol was added to partially solubilize the precipitate, and the reaction mixture was filtered and evaporated under reduced pressure. The residue was dissolved in 100 ml of ether and the ether solution was filtered and dried over 4A molecular sieves. The ether solution was evaporated under reduced pressure, giving the desired Mg salt as a light tan rubbery solid of the following elemental composition:

Calculated for $C_{44}H_{86}N_2O_8Mg$. Calculated : C, 66.43; H, 10.90; N, 3.52; Mg, 3.05. Found: C, 66.35; H, 10.75; N, 3.53; Mg, 2.66.

EXAMPLE 10

Ca(II)
Bis[O-mono(2,6-diethyl-2,3,6-trimethylpiperidyl-4)sebacate]

A. In a 125 ml erlenmeyer flask equipped with a magnetic stirrer were placed 3.84 g (0.01 moles) of O-mono(2,6-diethyl-2,3,6-trimethylpiperidyl-4)sebacate, 5 ml of 2N NaOH and 25 ml of water. The mixture was stirred for 1 hour at room temperature until the reaction became homogeneous. To the stirred solution was added portionwise a solution of 0.555 g (0.005 moles) of $CaCl_2$ in 5 ml of water. To the stirred solution was also added 50 ml of $CHCl_3$ and the reaction mixture was allowed to stir for 1 hour. The reaction mixture was transferred to a separatory funnel and the chloroform layer separated. The aqeous layer was washed with 50 ml of $CHCl_3$, the $CHCl_3$ extracts combined, dried over 4A molecular sieves, and evaporated under reduced pressure, giving the desired Ca salt as a light tan resin of the following elemental composition:

Calculated for $C_{44}H_{86}N_2O_8Ca$. Calculated: C, 65.14; H, 10.69; N, 3.45; Ca, 4.94. Found: C, 65.36; H, 10.18; N, 3.46; Ca, 4.75.

EXAMPLE 11

By following the procedure of Example 8(A) and substituting the following metal complexes for nickel chloride:

(a) manganese chloride
(b) zinc chloride
(c) cobalt(ous) chloride
(d) tin (IV) chloride there are respectively obtained:

(a) manganese complex of O-mono(2,6-diethyl-2,3,6-trimethylpiperidyl-4)sebacate
(b) zinc complex of O-mono(2,6-diethyl-2,3,6-trimethylpiperidyl-4)sebacate
(c) cobalt complex of O-mono(2,6-diethyl-2,3,6-trimethylpiperidyl-4)sebacate
(d) tin complex of O-mono(2,6-diethyl-2,3,6-trimethylpiperidyl-4)sebacate

EXAMPLE 12

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The test conducted on polymers using an artificial light exposure device is described below:

(a) Sample Preparation 5 mil Film—Unstabilized polypropylene powder (Hercules Profax 6501) is thoroughly blended with 0.5% by weight of O-mono(2',6'-diethyl-2',3',6'-trimethylpiperdyl-4) -2-methyl succinate and 0.2% by weight of dioctadecyl 3,5-di-t-butyl-4-hydroxybenzylphosphonate. The blended material is then milled on a two roll mill for 5 minutes at 182° C. The milled sheet is then compression molded at 220° C. into 5 mil thick film under a pressure of 175 psi and water cooled in the press.

(b) Testing Method

This test is conducted in a FS/BL unit, basically of the American Cyanamid design, which consists of 40 tubes of alternating fluorescent sunlamps and black lights (20 of each). The 5 mil sample film which are mounted on 3"×2" IR card holders with ¼"×1" windows are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

Polypropylene stabilized with the above hindered piperidine compound is found to be much more stable than the unstabilized polypropylene. Polypropylene is likewise stabilized when the following stabilizers are substituted for O-mono(2',6'-diethyl-2',3',6'-trimethyl piperidyl-4')2-methyl succinate in the procedures described above:

(a) Ni(II) Bis[O-mono(2',6'-diethyl-2',3',6'-trimethylpiperidyl-4')2-methylpiperidyl-4')2-methyl succinate]
(b) O-mono(2',6'-diethyl-2',3',6'-trimethylpiperidyl-4')3-methyl glutarate
(c) Mg(II) Bis[O-mono(2',6'-diethyl-2',3',6'-trimethylpiperidyl-4')3-methyl glutarate]
(d) Co(III) Bis[O-mono(2',6'-diethyl-2',3',6'-trimethylpiperidyl-4')3-methyl glutarate]
(e) Ca(II) Bis[O-mono(2',6'-diethyl-2', 3', 6'-trimethylpiperidyl-4')2-methyl succinate]
(f) O-mono(2,6-diethyl-2,3,6-trimethylpiperidyl-4 ) sebacate
(g) Ni(II) Bis[O-mono(2,6-diethyl-2,3,6-trimethyl piperidyl-4)sebacate]
(h) Mg(II) Bis[O-mono(2,6-diethyl-2,3,6-trimethyl piperidyl-4)sebacate]
(i) Ca(II) Bis[O-mono(2,6-diethyl-2,3,6-trimethyl piperidyl-4)sebacate]
(j) Ni(II) Bis[O-mono(2',6'-di-n-butyl-2',6'-dimethyl-3'-n-propyl piperidyl-4')2-methyl succinate]

Other hindered phenolic antioxidants may be used in place of di-octadecyl(3,5-di-t-butyl-4-hydroxybenzyl) phosphonate in the above mentioned compositions, for example, di-n-octadecyl α-(3-t-butyl-4-hydroxy-4-methylbenzyl)malonate, 2,4-bis-(n-octylthio)-6-(3,4-di-t-butyl-4-hydroxyaniline)-1,3,5-triazine, octadecyl 3-(3',5'-di-t-butyl-4'-hydroxyphenyl) propionate, pentaerythritol-tetrakis[3-(3,5-di-t-butyl-4-hydroxyphenyl)]-propionate, tris-(3,5-di-t-butyl-4-hydroxybenzyl) isocyanurate, 2,6-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzene and tris{2-[3-(3,5-di-tert-butyl-4-hydroxyphenyl)propionyloxy]ethyl}isocyanurate.

The above compositions are also stabilized when the following UV absorbers are included in the formulation at 0.01 to 2%.

(a) 2(2'-hydroxy-3', 5'-di-t-butylphenyl)-5-chlorobenzotriazole
(b) 2-hydroxy-4-methoxy-5-sulfobenzophenone trihydrate
(c) 2-hydroxy-4-n-oxtoxybenzophenone
(d) [2,2'-thiobis(4-t-octylphenolate)]-n-butylamine nickel II
(e) p-octylphenyl salicylate
(f) 2,2'-dihydroxy-4-4'-dimethoxybenzophenone
(g) 2(2'-hydroxy-5'-methylphenyl)-benzotriazole.

EXAMPLE 13

High impact polystyrene resin containing elastomer (i.e., butadiene-styrene) is stabilized against loss of elongation properties due to exposure to ultraviolet light by incorporation of 0.2% by weight of O-mono(2'-, 6'-diethyl-2',3',6'-trimethyl piperidyl-4')2-methyl succinate.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C. and a pressure of 2,000 pounds per square inch into sheets of uniform thickness (25 mil). The sheets are then cut into strips approximately 4×0.5 inches. A portion of these strips is then measured for percent of elongation in the Instron Tensile Testing Apparatus (Instron Engineering Corporation, Qunicy Massachusetts). The remaining portions of the strips are placed in an FS/Bl chamber according to Example 12(B) except that the samples are mounted on white cardboard stock and the time to 50% reduction in elongation is measured. The stabilized polystyrene resin retains its elongation property longer than the unstabilized resin.

EXAMPLE 14

Unstabilized linear polyethylene is solvent blended in methylene chloride with 0.5% by weight of the substrate of the nickel complex of O-mono(2,6-diethyl-2,3,6-trimethyl piperidyl-4)sabacate and the vacuum dried. The resin is then extrusion compounded on a 1 inch 24/1-L/D extruder, melt temperature 450° F. (232° C.) and pressed for 7 minutes at a temperature of 163° C. and a pressure of 2,000 psi into a sheet of uniform thickness of 100 mil. The sheets are then cut into plaques of 2 inch ×2 inch. The plaques are then exposed in an FS/BL exposure device and color measurements made periodically using a Hunter Color Difference Meter Model D25. Polyetheylene stabilized with the above compound is found to be much more stable than the unstabilized polyethylene or the polyethylene stabilized only with an antioxidant.

EXAMPLE 15

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution. To the emulsion is added 50 ml of 25% NaCl solution. A 6% NaCl solution adjusted with hydrochloric acid to a pH 1.5 is added in a thin stream with vigorous stirring. When ph 6.5 is reached, the rubber begins to coagulate and the addition is slowed down in order to maintain uniform agitation. The addition of the acidic 6% NaCl solution is terminated when a ph 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°–45° C.

The dried rubber (25 g) is heated under nitrogen at 125° C. in a Brabender mixer and to this is added with mixing 0.25 g (o.5%) of Co(II) bis[O-mono(2',6'-diethyl-2',3',6'-trimethylpiperidyl-4')3-methyl glutarate]. The composition is mixed for 5 minutes after which it is cooled and compression molded at 125° C. into 5"×0.025' plaques.

The plaqaues are exposed to an Xenon Arc weatherometer and the color measurement (L-b) is made after 45, 125 and 290 hours. The samples stabilized with the above compound are found to be much more light stable than the unstabilized samples.

EXAMPLE 16

To 50 g of polyacetal resin containing 0.1% of an acid scavenger, dicyandiamide, is added 0.2% by weight of Ca(II) bis[O-mono(2',6'-diethyl-2',3',6'-trimethylpiperidyl-4')-2-methyl succinate] and milled for 7 minutes at 200° C. in a Brabender Plasti-recorder. The milled formulation is subsequently pressed into a 40 mil sheet at 215° C. at 350 psi for 90 seconds then cooled quickly in a cold press at 350 psi. The stabilized sheets are then remolded for 2 minutes at contact pressure and for 3 minutes at 300 psi at 215° C. to give plaques 1½ inch×2½ inch×125 mil. Thereafter, the testing procedure of Example 13 is followed to determine the light stability of the samples. The stabilized samples are found to be more stable than the unstabilized samples.

EXAMPLE 17

Unstabilized thoroughly dried polyethylene terphthalate chips are dry blended with 1.0% of Mg(II) bis [O-mono(2,6-diethyl-2,3,6-trimethylpiperidyl-4) sebacate]. 60/10 denier multifilament melt spun at a melt temperature of 290° C. The oriented fiber is wound on white cards and exposed in an Xenon Arc Fadeometer. Color measurements are made periodically with a Hunter Color Difference Meter Model D25. The stabilized samples are found to be much more light stable than the unstabilized samples.

EXAMPLE 18

(a) A composition comprising acrylonitrile-butadiene-styrene terpolymer and 1% by weight of O-mono-(2,6-diethyl-2,3,6-trimethylpiperidyl-4) sebacate resists embrittlement due to exposure to ultraviolet light longer than one which does not contain the stabilizer.

(b) A composition comprising polyurethane prepared from toluene diisocyanate and alkylene polyols and 1.0% by weight of Ca(II) bis[O-mono-2,6-diethyl-2,3,6-trimethylpiperidyl-4) sebacate is more stable to sunlight, fluorescent sunlamps, black lights and fluorescent lights that the unformulated polyurethane.

(c) A composition comprising a polycarbonate prepared from bisphenol-A and phosgene and 1% by weight of Ni(II) bis [O-mono(2',6'-diethyl-2',3',6'-trimethyl-piperidyl-4')2-methyl succinate]resists discoloration due to exposure to ultraviolet light longer than one which does not contain the stabilizer.

(d) A composition comprising polymethylmethacrylate and 0.25% by weight of O-mono(2',6'-diethyl-2',3',6'-trimethylpiperidyl-4')thiodipropionate resists discoloration due to exposure to ultraviolet light longer than one which does not contain the stabilizer.

EXAMPLE 19

(a) A stabilized polyamide (nylon 6,6) is prepared by incorporating therein 0.1% of Ni(II) bis [O-mono(2',6'-diethyl-2',3',6'-trimethylpiperidyl-4')thiodiglycolate]. The light stability of the stabilized composition is superior to that of an unstabilized polyamide.

(b) A stabilized polyphenylene oxide polymer (prepared by polymerizing 2,6-dimethylphenol) is prepared by incorporating therein 0.5% by weight of Ni(II) bis-[O-mono(2,6-diethyl-2,3,6-trimethylpiperidyl-4)suberate]. The stabilized compositions resist embrittlement due to exposure to ultraviolet light longer than one which does not contain the stabilizer.

(c) A stabilized crystalline polystyrene is prepared by incorporating therein 0.1% weight of Ni(II) bis[O-mono(2',6'-di-n-butyl-2',6'-dimethyl-3'-n-propyl-piperidyl-4')2-methyl succinate]. The stabilized composition resists embrittlement due to exposure to ultraviolet light longer than one which does not contain the stabilizer.

Antioxidants may also be incorporated into each of the above mentioned compositions, for example, di-n-octadecyl-α,α'-bis(3-t-butyl-4-hydroxy-5-methylbenzyl) malonate, 2,4-bis(4-hydroxy-3,5-di-t-butylphenoxy)6-(n-octylthioethylthio)-1,3,5-triazine, 2,4-bis(3,5-di-t-butyl-hydroxyphenoxy)-6-(n-octylthio-1,3,5-triazine, di-n-octadecyl 3(3',5'-di-t-butyl-4-hydroxyphenyl)propionate, respectively.

The invention encompasses compounds having the formula $$\left( \begin{array}{c} R_5 \quad R_6 \quad R_7 \\ R_3-N \underset{R_1 \quad R_2 \quad R_8}{\bigtriangleup} -O-\underset{\|}{\overset{O}{C}}-R_4-\underset{\|}{\overset{O}{C}}-O \end{array} \right)_z M$$

In the above structure M is hydrogen or metal and may also be $M'(R)_n$ where R represent water, alcohols, glycols, diols, triols, tetraols, pentols, hexitols as well as ammonia, amines and amino alcohols. M' is a metal. In the case of M', z represents the primary value and n represents the coordination number of the metals.

The compounds wherein M is $M'(R)_n$ may be prepared by mixing equimolar ratios of the compounds containing M and the co-ligand R in an appropriate solvent, refluxing, and subsequently evaporating to dryness. More specifically, when M is Nickel and R is n-butylamine the compound may be suspended in isopropanol, the n-butylamine added, and the mixture refluxed until solution is achieved, then evaporated to dryness.

What is claimed is:

1. A compound of the formula $$\left( \begin{array}{c} R_5 \quad R_6 \quad R_7 \\ R_3-N \underset{R_1 \quad R_2 \quad R_8}{\bigtriangleup} -O-\underset{\|}{\overset{O}{C}}-R_4-\underset{\|}{\overset{O}{C}} \end{array} \right)_z M \qquad I$$

wherein $R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms β-methoxyethyl, alkenyl having 3 to 4 carbon atoms, propargyl, benzyl, benzyl substituted by 1 or 2 methyl groups or alkanoyl containing 1 to 18 carbon atoms.

$R_4$ is straight- or branched-chain alkylene having 1 to 8 carbon atoms, or the group $-(CH_2)_mY(CH_2)_n-$ wherein Y is oxygen or sulfur and m and n independently of each other are an integer from 1 to 3, M is hydrogen or metal selected from the group consisting of barium, calcium, magnesium, sodium, potassium, Z has a value of from 1 to 4, the value of Z being the same as the available valence of M, and either (a) $R_5$ is alkyl of 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen, or (b) $R_5$ and $R_6$ together with the carbon to which they are bound form a cyclopentyl or cyclohexyl ring, which is unsubstituted or substituted with a methyl group and $R_7$ and $R_8$ are independently hydrogen or alkyl of 1 to 5 carbon atoms.

2. A compound according to claim 1 wherein $R_1$ is straight- or branched-chain alkyl of 1 to 6 carbon atoms, $R_2$ is straight- or branched-chain alkyl of 2 to 6 carbon atoms, $R_5$ is alkyl of 2 to 6 carbon atoms, $R_6$ is alkyl of 1 to 6 carbon atoms, and $R_7$, and $R_8$ are independently hydrogen or alkyl of 1 to 5 carbon atoms; provided that $R_7$ and $R_8$ are not both hydrogen.

3. A compound according to claim 1 wherein $R_1$ and $R_6$ are methyl, $R_5$ is alkyl of 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen.

4. A compound according to claim 1 wherein $R_4$ is straight- or branched-chain alkylene having 1 to 8 carbon atoms.

5. A compound according to claim 1 wherein $R_4$ is the group $-(CH_2)_mY(CH_2)_n-$, wherein Y, m and n are as defined in claim 1.

6. A compound according to claim 1 wherein $R_4$ is straight-chain alkylene having 1 to 8 carbon atoms.

7. A compound according to claim 1 wherein M is selected from hydrogen.

8. A compound according to claim 1 which is O-mono(2',6'-diethyl-2',3',6'-trimethylpiperidyl-4')2-methyl succinate.

9. A compound according to claim 1 which is Ca(II) Bis[O-mono(2',6'-diethyl-2',3',6'-trimethyl-piperidyl-4')2-methyl succinate].

10. A compound according to claim 1 which is Mg(II) Bis[O-mono(2',6'-diethyl-2',3',6'-trimethylpiperidyl-4')3-methyl glutarate].

11. A compound according to claim 1 which is mg(II) Bis[O-mono(2,6-diethyl-2,3,6-trimethylpiperidyl-4)sebacate].

12. A compound according to claim 1 which is Ca(II) Bis[O-mono(2,6-diethyl-2,3,6-trimethylpiperidyl-4)sebacate].

13. A compound according to claim 1 which is O-mono(2',6'-diethyl-2',3',6'-trimethylpiperidyl-4) 3-methyl glutarate.

14. A compound according to claim 1 which is O-mono(2,6-diethyl-2,3,6-trimethylpiperidyl-4)sebacate.

15. A composition of matter stabilized against ultraviolet deterioration which comprises a synthetic organic polymer normally subject to ultraviolet deterioration containing from
 (a) 0.005% to 5% of a stabilizing compound according to claim 1,
 (b) 0 to 5% of a phenolic antioxidant,
 (c) 0 to 5% of a thio co-stabilizer, and
 (d) 0 to 5% of a U.V. absorber.

16. A composition of claim 15 wherein the organic material is a polyolefin.

17. A composition of claim 16 wherein the polyolefin is polypropylene.

* * * * *